US010076371B2

(12) United States Patent
Velikov et al.

(10) Patent No.: US 10,076,371 B2
(45) Date of Patent: Sep. 18, 2018

(54) ORTHOPEDIC PLATE

(71) Applicant: ZIMMER GMBH, Winterthur (CH)

(72) Inventors: Jordan Velikov, Horgen (CH); Thomas Teschke, Ruggel (LI)

(73) Assignee: Zimmer GmbH, Winterthur (CH)

( * ) Notice: Subject to any disclaimer, the term of this patent is extended or adjusted under 35 U.S.C. 154(b) by 336 days.

(21) Appl. No.: 14/783,270

(22) PCT Filed: Apr. 11, 2014

(86) PCT No.: PCT/EP2014/057432
§ 371 (c)(1),
(2) Date: Oct. 8, 2015

(87) PCT Pub. No.: WO2014/167115
PCT Pub. Date: Oct. 16, 2014

(65) Prior Publication Data
US 2016/0045234 A1    Feb. 18, 2016

(30) Foreign Application Priority Data

Apr. 12, 2013   (EP) .................................... 13163528

(51) Int. Cl.
*A61B 17/80*    (2006.01)
*A61B 17/70*    (2006.01)

(52) U.S. Cl.
CPC ...... *A61B 17/8085* (2013.01); *A61B 17/7059* (2013.01); *A61B 17/80* (2013.01)

(58) Field of Classification Search
CPC .................. A61B 17/8085; A61B 17/7059
See application file for complete search history.

(56) References Cited

U.S. PATENT DOCUMENTS 3,604,414 A * 9/1971 Borges ............... A61B 17/8009
606/105
4,338,926 A * 7/1982 Kummer ............... A61B 17/80
606/62

(Continued)

FOREIGN PATENT DOCUMENTS

DE    202005020490 U1    3/2006
EP         0052998 A1    6/1982
WO    WO-2014167115 A1   10/2014

OTHER PUBLICATIONS

"European Application Serial No. 14716606.0, Communication pursuant to Article 94(3) dated Nov. 24, 2016", 6 pgs.

(Continued)

*Primary Examiner* — Andrew Yang
(74) *Attorney, Agent, or Firm* — Schwegman, Lundberg & Woessner, P.A.

(57) ABSTRACT

The present disclosure provides an orthopedic plate, in particular a plate for osteosynthesis. The plate (31) comprising a body (33). The body (33) has a distal surface (15) adapted to be arranged facing the fractured bone and a proximal surface (13) adapted to be arranged facing away from the fractured bone. The surfaces (13, 15) define a distal and a proximal face of the plate (31), respectively. The body (33) further has a length measured along a longitudinal direction (23), a width measured along a transverse direction (51), and a thickness measured from the distal surface (15) to the proximal surface (13). The body (33) comprises two longitudinal plate ends (35) delimiting the body (33) in the longitudinal direction (23). The body (33) comprises at least one slotted longitudinal section (47). The slotted section (47) extends over a part of the length of the body (33), wherein within the slotted section (47) at least one slot (37) is arranged. The slot (37) extends in the transverse direction (51) of the body (33) such as to subdivide the body (33) in (Continued)

the slotted section (47) into at least two layers (39, 41) comprising at least a distal layer (41) facing the fractured bone and a proximal layer (39) facing away from the fractured bone. The at least one slot (37) is arranged between the distal layer (41) and the proximal layer (39).

22 Claims, 3 Drawing Sheets

(56) References Cited

U.S. PATENT DOCUMENTS

| | | | | |
|---|---|---|---|---|
| 5,681,312 | A * | 10/1997 | Yuan | A61B 17/7008 606/250 |
| 6,406,478 | B1 * | 6/2002 | Kuo | A61B 17/7059 606/295 |
| 8,900,620 | B2 * | 12/2014 | Fulmer | A61F 2/06 424/422 |
| 9,414,864 | B2 * | 8/2016 | Trieu | A61B 17/7059 |
| 2008/0154367 | A1 | 6/2008 | Justis et al. | |
| 2010/0179552 | A1 | 7/2010 | Wolter | |
| 2010/0249850 | A1 | 9/2010 | Cerynik et al. | |
| 2010/0268282 | A1 | 10/2010 | Trieu | |
| 2010/0274248 | A1 | 10/2010 | Overes et al. | |
| 2011/0218570 | A1 | 9/2011 | Felix et al. | |

OTHER PUBLICATIONS

"International Application Serial No. PCT/EP2014/057432, International Preliminary Report on Patentability dated Oct. 22, 2015", 9 pgs.

"International Application Serial No. PCT/EP2014/057432, International Search Report dated Sep. 1, 2014", 5 pgs.

"International Application Serial No. PCT/EP2014/057432, Written Opinion dated Sep. 1, 2014", 7 pgs.

"European Application Serial No. 14716606.0, Communication Under Rule 71(3) EPC dated Aug. 10, 2017", 27 pgs.

"European Application Serial No. 18150256.8, European Extended Search Report dated Apr. 18, 2018", 8 pgs.

\* cited by examiner

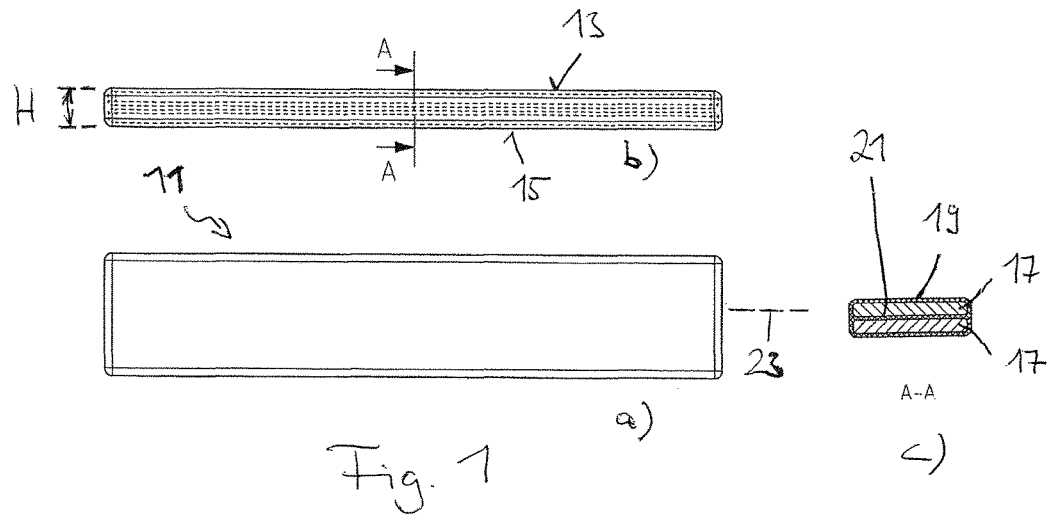
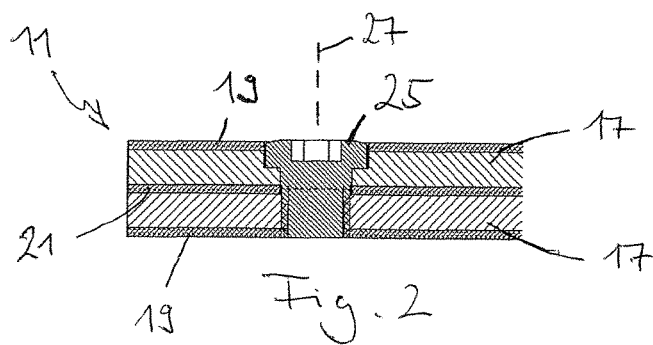
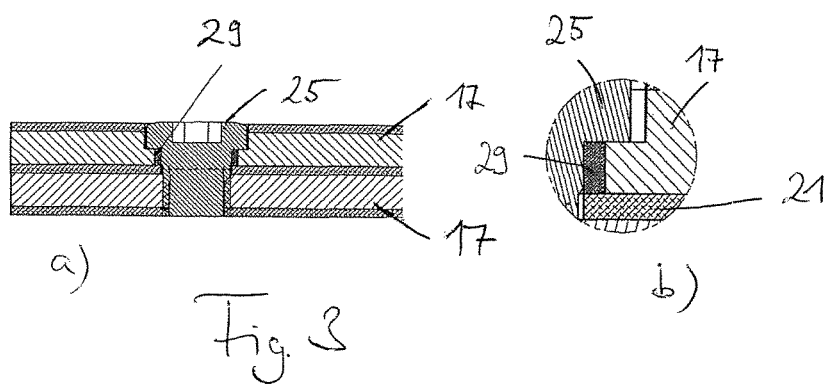

ORTHOPEDIC PLATE

This application is a U.S. National Stage Application under 35 U.S.C. 371 from International Application Serial No. PCT/EP2014/057432, filed on Apr. 11, 2014, and published as WO 2014/167115 A1 on Oct. 16, 2014, which claims priority to European Application No. 13163528.6, filed on Apr. 12, 2013, the benefit of priority of each of which is claimed hereby, and each of which are incorporated by reference herein in its entirety.

BACKGROUND

1. Field of the Disclosure

The present disclosure relates to orthopedic implants, and more particularly, to orthopedic plates, as described in the preambles of the independent claims.

2. Description of the Related Art

For the treatment of a bone fracture, the fracture may be fixed by means of pins, screws, wires or plates after alignment of the individual bone fragments in their correct positions (repositioning). In particular, an osteosynthetic plate can be used which is fastened to the individual bone fragments by means of screws to hold the individual bone fragments in a fixed position with respect to one another.

According to Wolff's law and stress shielding theory, decreasing the loading on a bone, e.g. by means of an osteosynthetic plate, leads to weakening of the bone. Attempts have been made to develop osteosynthetic plates that are less rigid.

SUMMARY

The present disclosure provides an orthopedic plate, in particular a plate for osteosynthesis. The plate comprises a body. The body has a distal surface adapted to be arranged facing the fractured bone and a proximal surface adapted to be arranged facing away from the fractured bone. The surfaces define a distal face and a proximal face of the plate, respectively. The body further has a length measured along a longitudinal direction, a width measured along a transverse direction, and a thickness measured from the distal surface to the proximal surface. The body comprises at least one slotted section, in particular slotted longitudinal section. The slotted section extends over a part of the length of the body, wherein within the slotted section at least one slot is arranged. The slot extends in the transverse direction of the body such as to subdivide the body in the slotted section into at least two layers, comprising at least a distal layer facing the fractured bone and a proximal layer facing away from the fractured bone. The at least one slot being is arranged between the distal layer and the proximal layer.

It has been found that such plates, while generally maintaining the same tensile stiffness as conventional plates, have a reduced bending stiffness, in particular with respect to a same unslotted body, and, thus, aid in stimulating remodeling of the bone.

Throughout the present application the positional terms "distal" and "proximal" will be used to describe a direction away from (distal) and toward (proximal) a surgeon of the orthopedic plate when implanting it, respectively.

Generally, the distal surface may be concave, in particular in a cross section of the body and/or the proximal surface may be convex, in particular in a cross section of the body. In particular, the longitudinal direction and the transverse direction are at least substantially perpendicular to each other. The body may comprise one slotted section or a plurality of slotted sections. A slotted section may comprise one slot or a plurality of slots. In particular, in case of a plurality of slots, when referring to "the slot" hereinafter, this should be understood as "at least one of the slots". In particular, the term "longitudinal section" may denote that said section has a certain extent in the longitudinal direction.

In an aspect, the slot, when viewing the plate in the transverse direction, is at least essentially parallel to the longitudinal direction. In another aspect, the slot, when viewing the plate in the transverse direction, is at least essentially aligned with the local longitudinal extent of the plate in the slotted section. Thus, in case the body is curved, when viewing the plate along a longitudinal direction, the slot may follow the curvature of the body and/or the body and the slot may be parallel to each other locally and/or the longitudinal extent of the body and the longitudinal extent of the slot may be parallel at a respective location.

In an aspect, the slot is arranged such that the slot does not penetrate any of the proximal or distal surfaces. In particular, with respect to the longitudinal direction of the plate, the slot may, however, penetrate at least one of the lateral surfaces of the body and/or at least one of the front and back surfaces of the body. In an aspect, the slot is open laterally, in particular in a direction perpendicular to the longitudinal direction, and in particular in the transverse direction. The slot, however, does not have to be open laterally. Also in case of a laterally non-open slot, the slot extends along the width of the body such as to subdivide the body in the slotted section into the at least two layers. In an aspect, the slot is arranged between the distal surface and the proximal surface. In particular, the slot may not intersect any of the distal and proximal surfaces.

In an aspect, the slot is at least substantially planar and/or extends in a plane defined by the longitudinal direction and the transversal direction. In particular, the slot may be at least substantially planar although the body is curved, in particular although the body has a convex proximal surface and/or concave distal surface. In an alternate embodiment, the slot may be curved.

In an aspect, the slot extends from at least one plate end in a direction towards the other plate end and is open at the longitudinal plate end, and in particular at least one slot extends from each of the two plate ends in a direction towards the respective opposite plate end and is open at the respective plate end. This may result in a higher bending stiffness in a middle section of the plate than at the plate end(s). In another aspect, the slot is arranged between the longitudinal plate ends and is closed in the longitudinal direction. In particular, the body is slotted in a section arranged between the two plate ends of the plate.

In an aspect, the thickness of the body tapers towards at least one of the plate ends. This may result in a higher bending stiffness in a middle section of the plate than at the plate end(s) also.

In an aspect, the body is encased in a sheath or casing. The sheath may be made of a polymer material and/or comprise and/or consist of a bioresorbable material. The body may be made of a metal, metal alloy, fiber-reinforced plastic, non-resorbable polymer or any other material conceived suitable by the skilled person.

In an aspect, the plate comprises tensioning means suited to cause and/or maintain a tension of at least one layer arranged in a slotted section. In particular, the tensioning means are suited to cause and/or maintain a bending of the layer relative to the further parts of the body along a proximal-distal direction. In particular, the at least two layers are tensionable or pre-tensionable, respectively, relative to each other by the tensioning means.

The tensioning means may comprise at least one of adjustment means for adjustably and/or variably tensioning the layer and/or time dependent means for providing a time-dependent tensioning. The adjustment means may include an adjustment screw. The time dependent means may include a bioresorbable material.

In an aspect, the tensioning means comprise a thread provided in at least one layer, in particular the proximal layer, and a screw for being screwed into said thread, said thread being arranged such that the screw, when inserted into and advanced within the thread, abuts a further layer, in particular a distal layer. If, after abutting the further layer, the screw is further advanced within the thread, a force is applied between the at least two layers and the at least two layers are tensioned relative to each other, in particular by locally increasing a distance between the at least two layers. Such means may be suited to be operated interoperatively, that is, the surgeon may adjust the tensioning at his discretion.

In an aspect, the tensioning means comprise a thread provided in at least one layer, in particular a distally disposed layer, a through hole provided in at least one further layer, in particular proximally disposed layer, and a screw, the screw comprising a head and a shank, the shank comprising a male threaded section for being screwed into said thread, wherein the through hole has a minimum cross section, in particular a smallest diameter, larger than the maximum cross section of the screw shank and the male thread and smaller than the maximum cross section of the screw head such that the screw head may bear on a rim of the through hole when the screw shank is fed through the through hole and the male thread is screwed into and advanced within the threaded hole. Thus, the shank of the screw may be fed through the through hole, whereas the head of the screw abuts a surface of the further layer or a countersink provided in said surface. The at least two layers may thus be tensioned relative to each other, in particular by locally decreasing a distance between the at least two layers. Such means may also be operated interoperatively.

The tensioning means may also comprise a rivet or a screw-nut-combination connecting the at least two layers. Additionally or alternatively, the tensioning between the two layers may be provided by a bone screw.

In an aspect, the tensioning means or fixing means comprise a thread in each of at least two layers, the threads being axially aligned with each other, and a screw or an at least partly threaded stud for being threaded into each of the at least two threads.

Generally, an adjustable tensioning means which allows interoperative operation may provide the surgeon with a greater flexibility in the treatment of the fracture.

In an aspect, a bioresorbable material is disposed between a tensioning means and at least one of the layers. In particular, the bioresorbable material is provided in the form of a ring or a sleeve. A male tensioning means may be at least partly received in a sleeve comprising a bioresorbable material, wherein the sleeve is in particular arranged between a male tensioning element and a layer. In particular, a tensioning means comprises or consists of a bioresorbable material. In particular, a screw or a rivet may comprise or consist of a bioresorbable material. A bonding layer comprising a bioresorbable material may be provided between at least two layers such as to maintain and retardedly release a pre-applied tensioning between the two layers The bioresorbable material can be broken down by the body, i.e. will gradually resorb and be cleared from the body. Thus, the mechanical properties of the plate such as bending stiffness may be time-dependent. In particular, more and more load initially borne by the implant may be transferred to the bone.

The present disclosure further relates an orthopedic plate system, in particular a plate system for osteosynthesis, comprising at least two single plates stacked on top of each other, wherein the single plates are connected to each other via a common sheath and/or a bonding layer arranged between the at least two plates and/or via fixing means such as a fixing element and/or a fixation assembly fixing the at least two plates to each other. Such a plate system may exhibit the same technical effect as the orthopedic plate described above.

In an aspect, at least one of the common sheath and the bonding layer comprises a bioresorbable material. In an aspect, the fixing element comprises a bioresorbable material and/or the fixation assembly comprises an element, said element in turn comprising a bioresorbable material. The fixing element or fixation assembly may be a clamp, a rivet or a screw, for example. The rivet and the screw may, for example, comprise or consist of a bioresorbable material or be seated in a sleeve made of a bioresorbable material.

In an aspect, the plate or plate system includes a plurality of through holes extending from a proximal surface to a distal surface of the plate or plate system and adapted to receive bone anchoring elements, in particular bone screws, and defining an axial direction. In particular, the two single plates are fixable to each other and/or at least one layer of the plate is tensionable by the bone anchoring elements.

The present disclosure further relates to an implant set comprising at least one of an orthopedic plate or orthopedic plate system as described in this disclosure and a plurality of bone anchoring elements.

The present disclosure provides an orthopedic plate, in particular an osteosynthetic plate, comprising a body partly slotted in-plane to form an at least two-layered structure. The body is provided with at least one slot. In particular, the two layers are detached from each other in the slotted section, in particular form an interface therebetween. In particular, at least one of the slots is a through slot, i.e. extends over the entire width of the longitudinal body. In an aspect, the body of the plate has two plate ends in a longitudinal direction of the plate, wherein the plate is slotted from at least one plate end inwardly, in particular from each of the two plate ends inwardly. Alternatively or additionally, the plate may, however, also be slotted in a section between the two plate ends of the plate. Further, the body of the plate may include multiple slots. In another aspect, the body is encased in an envelope or casing. The envelope or casing may be made of a polymer material. In yet another aspect, the two layers are pre-tensionable relative to each other in a direction normal to an in-plane extension of the plate by bending the two layers relative each other. The two layers may be variably pre-tensionable relative each other. The pre-tension may be provided by at least one pre-tensioning element such as a drive screw or a bone screw for attaching the plate to a bone. In another aspect, in a slotted section, at least one hole is provided penetrating a proximal layer, wherein the at least one drive screw is threadable into the at least one hole such that a tip of the drive screw bears on a distal layer to bend the proximal layer relative to the distal layer. The present disclosure further relates to an orthopedic plate system, in particular an osteosynthetic plate system, comprising at least two single plates stacked on top of each other, wherein the single plates are connected to each other via a common envelope or casing. In an aspect, the envelope includes an intermediate layer arranged between the two single plates. In another aspect, the two single plates are fixed to each other. The fixation may be provided by at least one fixation element such as a fixing screw or a bone screw. In yet another aspect, the fixation and/or pre-tensioning of the two single plates and/or the two layers of the plate includes a bioresorbable material. The bioresorbable material may be interfaced between a pre-tensioning element and a proximal layer, in particular may be provided in the form of a ring or a sleeve. In still another aspect, the plate or plate system includes a plurality of through holes extending from the proximal surface to the distal surface of the plate or plate system and adapted to receive bone anchoring elements such as bone screws and defining an axial direction, wherein the two single plates and/or the two layers of the plate are fixable to each other and/or pre-tensionable to each other by the bone anchoring elements. The present disclosure further relates to an implant system comprising a plate or plate system in accordance with the above description and a plurality of bone anchoring elements.

It will be appreciated that the specific features of the embodiments described above can be combined. Thus any combinations of the features described in the dependent claims are disclosed herein, be they explicitly mentioned or not.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein:

FIG. 1a is a top view of an osteosynthetic plate according to an exemplary embodiment of the present disclosure.

FIG. 1b is a side view of the osteosynthetic plate of FIG. 1a.

FIG. 1c is a cross-sectional view of the osteosynthetic plate of FIG. 1b along line A-A.

FIG. 2 is a fragmentary cross-sectional view of an osteosynthetic plate according to another exemplary embodiment of the present disclosure.

FIG. 3a is a fragmentary cross-sectional view of an osteosynthetic plate according to another exemplary embodiment of the present disclosure.

FIG. 3b is a detail of the osteosynthetic plate of FIG. 3a.

Corresponding reference characters indicate corresponding parts throughout the several views. The exemplifications set out herein illustrate preferred embodiments of the disclosure and such exemplifications are not to be construed as limiting the scope of the disclosure in any manner.

DETAILED DESCRIPTION

Figure 4:
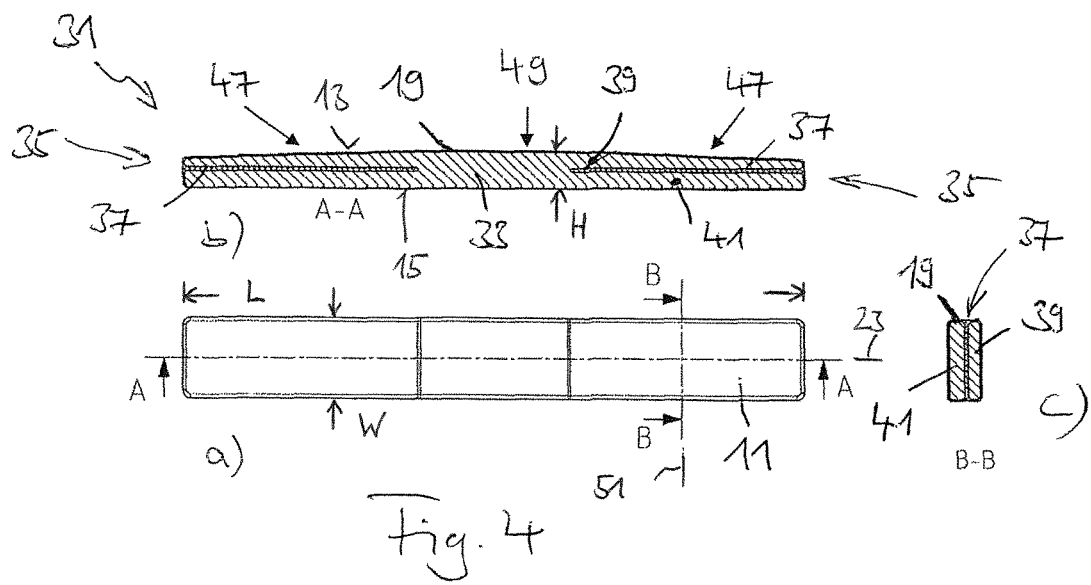
FIG. 4a is a top view of an osteosynthetic plate according to another exemplary embodiment of the present disclosure.
FIG. 4b is a cross-sectional view of the osteosynthetic plate of FIG. 4a along line A-A.
FIG. 4c is a cross-sectional view of the osteosynthetic plate of FIG. 4a along line B-B.

Referring to FIG. 1, osteosynthetic plate system 11 is shown and forms an elongate body including a proximal side or proximal surface 13 and a distal side or distal surface 15. The distal surface 15 is adapted to be arranged facing a fractured bone and the proximal surface 13 is adapted to be arranged facing away from the fractured bone. The osteosynthetic plate system 11 comprises two single plates 17 stacked on top of each other and thus a plate stack. The two plates 17 are hold together by a common envelope or sheath 19 encasing the two plates 17. An intermediate layer or bonding layer 21 is provided between the two plates 17. The bonding layer 21 is formed integral with the sheath 19. The sandwich plate system 11 may be used in treatment of bone fractures, for example. The osteosynthetic plate system 11 has a total height or total thickness of H. The osteosynthetic plate system 11 includes multiple through holes (not shown) arranged in row along a longitudinal axis or longitudinal direction 23 of the elongate osteosynthetic plate 11 system to hold bone screws for fastening the osteosynthetic plate system 11 to the bone or bone fractures, respectively.

By using the plate system 11 of thickness H comprising the two plates 17, the bending stiffness may be reduced compared to a single plate of thickness H. Thus, the present osteosynthetic plate system beneficially assists in stimulating the bone to remodel itself over time.

Referring to FIG. 2, the osteosynthetic plate system 11 is stiffened by fixing the two single plates 17 to each other by a fixing screw 25. For this purpose, the plate system 11 includes a through hole which extends through both plates 17 in axial direction 27 normal to the proximal surface 13 of the plate system 11. The fixing screw 25 extends all the way from the proximal surface 13 to the distal surface 15 and ends flush with the proximal and distal surfaces 13, 15. A threaded shaft of the fixing screw 25 engages a mating through hole thread of the distal plate 17 and a head of the fixing screw 25 pulls the proximal plate 17 towards the distal plate 17.

Referring to FIG. 3, a bioresorbable element 29 is interfaced between the fixing screw 25 and the proximal plate 17. Thus, the contact between the fixing screw 25 and the proximal plate 17 loosens over time. This results in a change of the bending stiffness of the plate system 11 over time. In particular, the bending stiffness decreases. Thus, the load that has to be borne by the bone increases over time to further stimulate the bone to remodel itself. In an alternate embodiment, the fixing screw 25 itself may comprise or consist of a bioresorbable material.

Referring to FIG. 4, osteosynthetic plate 31 is shown and comprises an integral elongate body 33 that is partly slotted from both plate ends 35 inwardly. The plate ends 35 delimit the body 33 in the longitudinal direction 23. Each of the two slots 37 extends in-plane of the plate 31. Thus, the plate 31 having a length L comprises two slotted end zones 47 and an unslotted middle zone 49. The length L is measured along the longitudinal direction 23 of the body 33. In particular, each of the two slotted end zones 47 represents a slotted section of the plate 31 extending over a part of the length L of the body 33. Each of the slots 37 extends over and/or spans the entire width W of the longitudinal body 33. The width W is measured along the transverse direction 51 of the body 33. The transverse direction 51 is at least essentially perpendicular to the longitudinal direction 23. Each of the slots 37 is open at both lateral sides of the longitudinal body 33 and at the respective longitudinal plate end 35. Each of the slots 37 is at least substantially planar and extends parallel to the distal surface 15 of the body 33, when viewing the plate 31 in the transverse direction 51 as shown in FIG. 4b. The slots 37 neither penetrate the proximal surface 13 nor the distal surface 15 of the body 33. The proximal surface 15 and the distal surface 13 define distal and proximal faces of the plate 31. Due to the slots 37, each of the end zones 47 forms a proximal layer 39 and a distal layer 41 arranged above each other and detached from each other. Thus, in the slotted sections 47, the body 33 is subdivided by the slots 37 into the layers 39, 41. The slots 37 form an interface between the two layers 39, 41. In the slotted section, the two layers 39, 41 are spaced apart from each other by a distance. The space between the two layers 39, 41 may be a free space. In another embodiment, the space between the two layers 9, 41 may be filled with an intermediate layer. The thickness H of the body 33, in particular the proximal surface 13, tapers towards both ends 35 of the plate 31. The thickness H of the body 33 is measured from the distal surface 15 to the proximal surface 13 of the body 33. The sandwich plate 31 is encased by a sheath 19 which, however, is optional and may also be omitted. The proximal layer 39 is that layer that faces the surgeon during surgery. Bone screws are inserted from proximal to distal. In general, a slotted section may be a slotted longitudinal section and/or a longitudinal slotted section.

Figure 5:
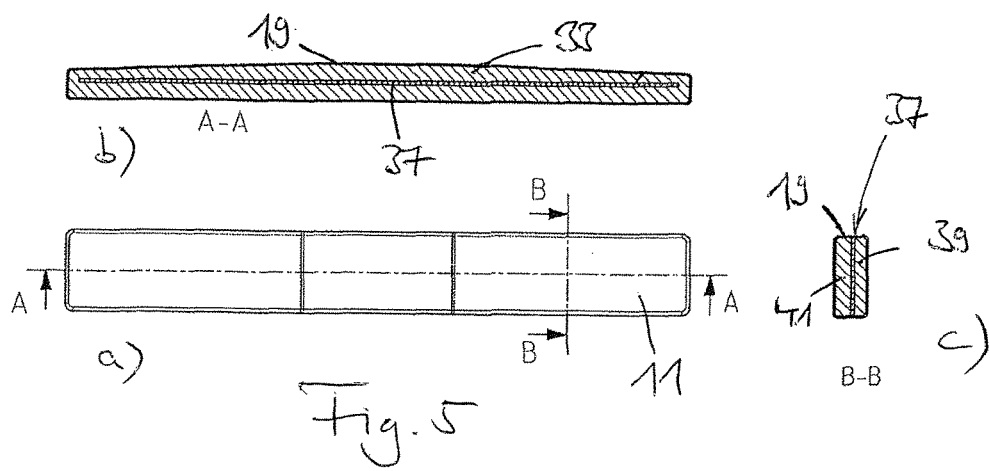
FIG. 5a is a top view of an osteosynthetic plate according to another exemplary embodiment of the present disclosure.
FIG. 5b is a cross-sectional view of the osteosynthetic plate of FIG. 5a along line A-A.
FIG. 5c is a cross-sectional view of the osteosynthetic plate of FIG. 5a along Line B-B.
Figure 6:
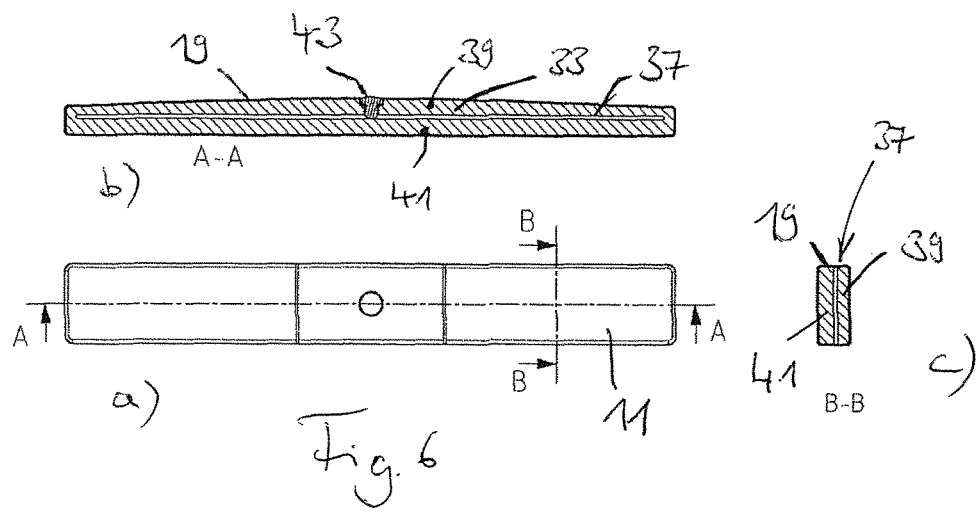
FIG. 6a is a top view of an osteosynthetic plate according to another exemplary embodiment of the present disclosure.
FIG. 6b is a cross-sectional view of the osteosynthetic plate of FIG. 6a along line A-A.
FIG. 6c is a cross-sectional view of the osteosynthetic plate of FIG. 6a along Line B-B.

Alternatively, as shown in FIG. 5, the osteosynthetic plate 31 may comprise a single slot 37 in a middle zone between the two plate ends 35. Referring to FIG. 6, a screw 43 such as a drive screw is threaded into a hole, in particular into a threaded hole, provided in the middle zone in the proximal layer 39 only. A tip of the screw 43 bears on or abuts the distal layer 41 so that the proximal layer 39 may be bended and thus tensioned or pre-tensioned relative to the distal layer 41. Thus, the screw 43 causes and maintains a tension and a bending of the proximal layer 39 relative to the distal layer 41. The extent of tension and bending depends upon how far the screw 43 is advanced into the hole. Thus, the screw 43 functions as an adjustment means for variably tensioning the two layers 39, 41 relative to each other. Sheath 19 may also be omitted in the embodiments of FIGS. 5 and 6. In another embodiment, a bioresorbable element in the form of a sleeve or such may be interfaced between the screw 43 and the proximal layer 39 as described above in connection with the fixing screw 25.

Figure 7:
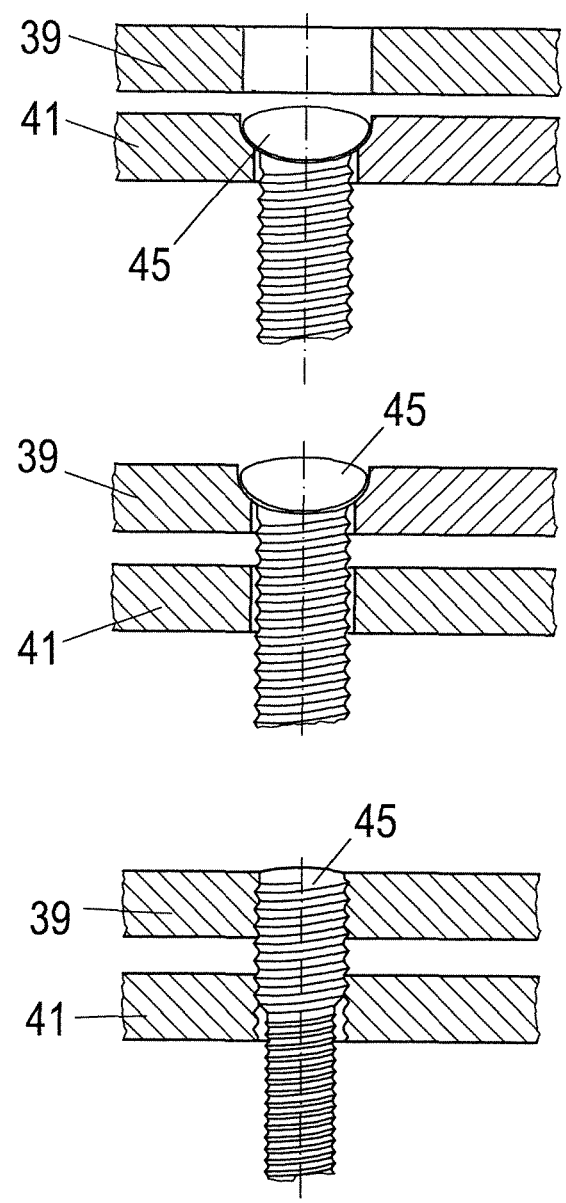
FIG. 7 shows fragmentary cross-sectional views of osteosynthetic plates according to other exemplary embodiments of the present disclosure.

FIG. 7 shows that a bone screw 45 for attaching the plate to a bone may be designed such that a head of the bone screw 45 contacts the distal layer 41 (top drawing), the proximal layer 39 (middle drawing) or both layers 39, 41 (bottom drawing). In the top drawing, the plate is fastened to the bone by the bone screw 45 via the distal layer 41. The corresponding through hole has a diameter which is larger in the proximal layer 39 than in the distal layer 41 such that the shaft of the bone screw 45 is feedable through both through hole sections, whereas the head of the bone screw 45 is feedable through the proximal through hole section only and abuts a countersink provided in the proximal surface of the distal layer 41. In the middle drawing, the plate is fastened to the bone by the bone screw 45 via the proximal layer 39. The corresponding through hole has a constant diameter such that the shaft of the bone screw 45 is feedable through both through hole sections, whereas the head of the bone screw 45 is not feedable through the through hole and abuts a countersink provided in the proximal surface of the proximal layer 39. In addition, the proximal layer 39 is tensioned with respect to the distal layer 41 by the bone screw 45. In the bottom drawing, the plate is fastened to the bone by the bone screw 45 via both layers 39, 41. The corresponding through hole has a constant diameter such that the shaft of the bone screw 45 is feedable through both through hole sections. The head of the bone screw 45 is provided with an external thread and the through hole is provided with an internal thread such that the head of the bone screw 45 is threadable into the through hole at both through hole sections.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

| Reference Numeral List | |
|---|---|
| 11 | osteosynthetic plate system |
| 13 | proximal surface |
| 15 | distal surface |
| 17 | single plate |
| 19 | sheath, casing |
| 21 | bonding layer |
| 23 | longitudinal direction |
| 25 | fixing screw |
| 27 | axial direction |
| 29 | bioresorbable element |
| 31 | osteosynthetic plate |
| 33 | body |
| 35 | plate end |
| 37 | slot |
| 39 | proximal layer |
| 41 | distal layer |
| 43 | screw |
| 45 | bone screw |
| 47 | slotted zone |
| 49 | unslotted zone |
| 51 | transverse direction |
| H | thickness |
| L | length |
| W | width |

The invention claimed is:
1. An orthopedic plate, in particular a plate for osteosynthesis, the plate comprising a body,
the body having a distal surface adapted to be arranged facing the fractured bone and a proximal surface adapted to be arranged facing away from the fractured bone, said surfaces defining a distal face and a proximal face of the plate, respectively, the body further having a length measured along a longitudinal direction, a width along a transverse direction, and a thickness measured from the distal surface to the proximal surface, the body comprising two longitudinal plate ends delimiting the body in the longitudinal direction,
wherein the body comprises a slotted longitudinal section, the slotted longitudinal section extending over a part of the length of the body, wherein within the slotted longitudinal section a slot is arranged, the slot extending in the transverse direction of the body such as to subdivide the body in the slotted longitudinal section into at least two layers comprising at least a distal layer facing the fractured bone and a proximal layer facing away from the fractured bone, the slot being arranged between the distal layer and the proximal layer, wherein the slot is open laterally and the slot is at least substantially planar, and wherein the slot extends from each of the two longitudinal plate ends towards the respective opposite plate end and is open at the respective plate end.

2. An orthopedic plate in accordance with claim 1, wherein the slot, when viewing the plate in the transverse direction, is at least essentially parallel to the longitudinal direction.

3. An orthopedic plate in accordance with claim 2, wherein the slot, when viewing the plate in the transverse direction, is at least essentially aligned with the local longitudinal extent of the plate in the slotted longitudinal section.

4. An orthopedic plate in accordance with claim 1, wherein the slot is arranged such that the slot does not penetrate any of the proximal or distal surfaces.

5. An orthopedic plate in accordance with claim 1, wherein the slot is arranged between the distal surface and the proximal surface.

6. An orthopedic plate in accordance with claim 1, wherein the thickness of the body tapers towards at least one of the plate ends.

7. An orthopedic plate in accordance with claim 1, wherein the body is encased in a sheath, the sheath being made of a polymer material and/or comprising a bioresorbable material.

8. An orthopedic plate in accordance with claim 1, wherein the plate comprises tensioning means suited to cause and/or maintain a tension of at least one layer arranged in the slotted longitudinal section, in particular suited to cause and/or maintain a bending of the at least one layer relative to further parts of the body along a proximal-distal direction.

9. An orthopedic plate in accordance with claim 8, wherein the tensioning means comprise at least one of the following: adjustment means for variably tensioning the layer and/or time dependent means for providing a time-dependent tensioning.

10. An orthopedic plate in accordance with claim 8, the tensioning means comprise a thread provided in at least one layer, in particular the proximal layer, and a screw for being screwed into said thread, said thread being arranged such that the screw, when inserted into and advanced within the thread, abuts a further layer, in particular a distal layer.

11. An orthopedic plate in accordance with claim 8, wherein the tensioning means comprise a thread provided in at least one layer, in particular a distally disposed layer, a through hole provided in at least one further layer, in particular a proximally disposed layer, and a screw, the screw comprising a head and a shank, the shank comprising a male threaded section for being screwed into said thread, wherein the through hole has a minimum cross section, in particular a smallest diameter, larger than the maximum cross section of the screw shank and the male thread and smaller than the maximum cross section of the screw head such that the screw head may bear on a rim of the through hole when the screw shank is fed through the through hole and the male thread is screwed into and advanced within the threaded hole.

12. An orthopedic plate in accordance with claim 8, wherein the tensioning means comprise a rivet connecting the at least two layers.

13. An orthopedic plate in accordance with claim 8, wherein the tensioning means comprise a thread in each of at least two layers, the threads being axially aligned with each other, and a screw or an at least partly threaded stud for being threaded into each of the at least two threads.

14. An orthopedic plate in accordance with claim 8, wherein a bioresorbable material is disposed between a tensioning means and at least one of the layers, and wherein the bioresorbable material is in particular provided in the form of a ring or a sleeve.

15. An orthopedic plate in accordance with claim 8, wherein a male tensioning means is at least partly received in a sleeve comprising a bioresorbable material, wherein the sleeve is in particular arranged between a male tensioning element and a layer.

16. An orthopedic plate in accordance with claim 8, wherein a tensioning means comprises a bioresorbable material.

17. An orthopedic plate in accordance with claim 16, wherein a bonding layer comprising a bioresorbable material is provided between at least two layers such as to maintain and retardedly release a pre-applied tensioning between the two layers.

18. An orthopedic plate system, in particular a plate system for osteosynthesis, comprising at least two single plates stacked on top of each other, wherein the single plates are connected to each other via a common sheath;

wherein the plate system includes a plurality of through holes extending from a proximal surface to a distal surface of the plate system and adapted to receive a bone anchoring element, wherein the plurality of through holes comprises:

a proximal through bore in a proximal of the at least two single plates, the proximal through bore having a first diameter; and a distal through bore in a distal of the at least two single plates, the distal through bore having a second diameter;

wherein the proximal through bore and the distal through bore are threaded;

wherein the first diameter and the second diameter are equal; and wherein the bone anchoring element comprises a shank and a head connected to the shank, wherein the head is configured to threadedly engage both the proximal through bore and the distal through bore.

19. An orthopedic plate system in accordance with claim 18, wherein the common sheath comprises a bioresorbable material.

20. An orthopedic plate system in accordance with claim 18, further comprising a fixing element for fixing the at least two plates to each other.

21. An orthopedic plate, in particular a plate for osteosynthesis, the plate comprising a body, the body having a distal surface adapted to be arranged facing the fractured bone and a proximal surface adapted to be arranged facing away from the fractured bone, said surfaces defining a distal face and a proximal face of the plate, respectively, the body further having a length measured along a longitudinal direction, a width along a transverse direction, and a thickness measured from the distal surface to the proximal surface, the body comprising two longitudinal plate ends delimiting the body in the longitudinal direction, wherein the body comprises a slotted longitudinal section, the slotted longitudinal section extending over a part of the length of the body, wherein within the slotted longitudinal section a slot is arranged, the slot extending in the transverse direction of the body such as to subdivide the body in the slotted longitudinal section into at least two layers comprising at least a distal layer facing the fractured bone and a proximal layer facing away from the fractured bone, the slot being arranged between the distal layer and the proximal layer, wherein the plate comprises tensioning means suited to cause and/or maintain a tension of at least one layer arranged in the slotted longitudinal section, in particular suited to cause and/or maintain a bending of the at least one layer relative to further parts of the body along a proximal-distal direction, and wherein a tensioning means comprises a bioresorbable material.

22. An orthopedic plate, in particular a plate for osteosynthesis, the plate comprising a body, the body having a distal surface adapted to be arranged facing the fractured bone and a proximal surface adapted to be arranged facing away from the fractured bone, said surfaces defining a distal face and a proximal face of the plate, respectively, the body further having a length measured along a longitudinal direction, a width along a transverse direction, and a thickness measured from the distal surface to the proximal surface, the body comprising two longitudinal plate ends delimiting the body in the longitudinal direction, wherein the body comprises a slotted longitudinal section, the slotted longitudinal section extending over a part of the length of the body, wherein within the slotted longitudinal section a slot is arranged, the slot extending in the transverse direction of the body such as to subdivide the body in the slotted longitudinal section into at least two layers comprising at least a distal layer facing the fractured bone and a proximal layer facing away from the fractured bone, the slot being arranged between the distal layer and the proximal layer, wherein the slot is open laterally and the slot is at least substantially planar, and wherein the slot is arranged between the longitudinal plate ends and is closed in the longitudinal direction.

* * * * *